United States Patent
Alfano et al.

(10) Patent No.: US 6,346,101 B1
(45) Date of Patent: *Feb. 12, 2002

(54) PHOTON-MEDIATED INTRODUCTION OF BIOLOGICAL MATERIALS INTO CELLS AND/OR CELLULAR COMPONENTS

(75) Inventors: Robert R. Alfano, Bronx; Cheng Hui Liu, Flushing, both of NY (US)

(73) Assignee: Research Foundation of City College of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/887,196

(22) Filed: Jun. 4, 1997

Related U.S. Application Data

(63) Continuation of application No. 08/584,695, filed on Jan. 11, 1996, now abandoned, which is a continuation of application No. 08/193,565, filed on Jul. 19, 1993, now abandoned.

(51) Int. Cl.$^7$ ............................................. A61B 18/18
(52) U.S. Cl. .............................. 606/15; 606/1; 606/10; 606/13; 606/17; 604/19; 604/20; 128/898
(58) Field of Search ............... 606/2, 3–19; 604/14–22; 128/898

(56) References Cited

U.S. PATENT DOCUMENTS 4,309,998 A * 1/1982 Aron nee Rosa et al. ...... 606/6
5,061,265 A * 10/1991 Abela et al. .................... 606/7
5,246,437 A * 9/1993 Abela ........................... 606/17

OTHER PUBLICATIONS

Trokel; "YAG Laser Ophthalmic Microsurgery"; Appleton–Century–Eroft/Norwalk, Ct. pp. 40–41.*

* cited by examiner

Primary Examiner—David M. Shay
(74) Attorney, Agent, or Firm—Kriegsman & Kriegsman

(57) ABSTRACT

A photon-mediated technique for introducing biological materials into cells and/or cellular components. The technique may be used to introduce nucleic acids, such as DNA and RNA, proteins or other biological materials into mammalian cells (as well as into other animal and plant cells), which materials may then flow into the nuclei of the cells. The technique uses picosecond or femtosecond light pulses propagating in the UV, visible and near infrared wavelength regions with powers on the order of $1 \times 10^{10}$ W/cm$^2$. In practice, the desired biological materials are coated on the end of the inner core of a single mode fiber or the ring core of a fiber in a fiber array. Each fiber is sized to correspond to one cell, with the core size ranging from $2\mu$ to $10\mu$, and the cladding ranging from $10\mu$ to $30\mu$. The laser pulse travels through a fiber core which is coated with the materials and ablates a portion of a targeted cell or cellular component membrane. In addition, as the laser pulse exits the fiber, it imparts energy and momentum to the materials applied to the end of the fiber. Consequently, after ablation of a portion of the membrane, some of the biological materials are caused to enter therethrough.

2 Claims, 6 Drawing Sheets

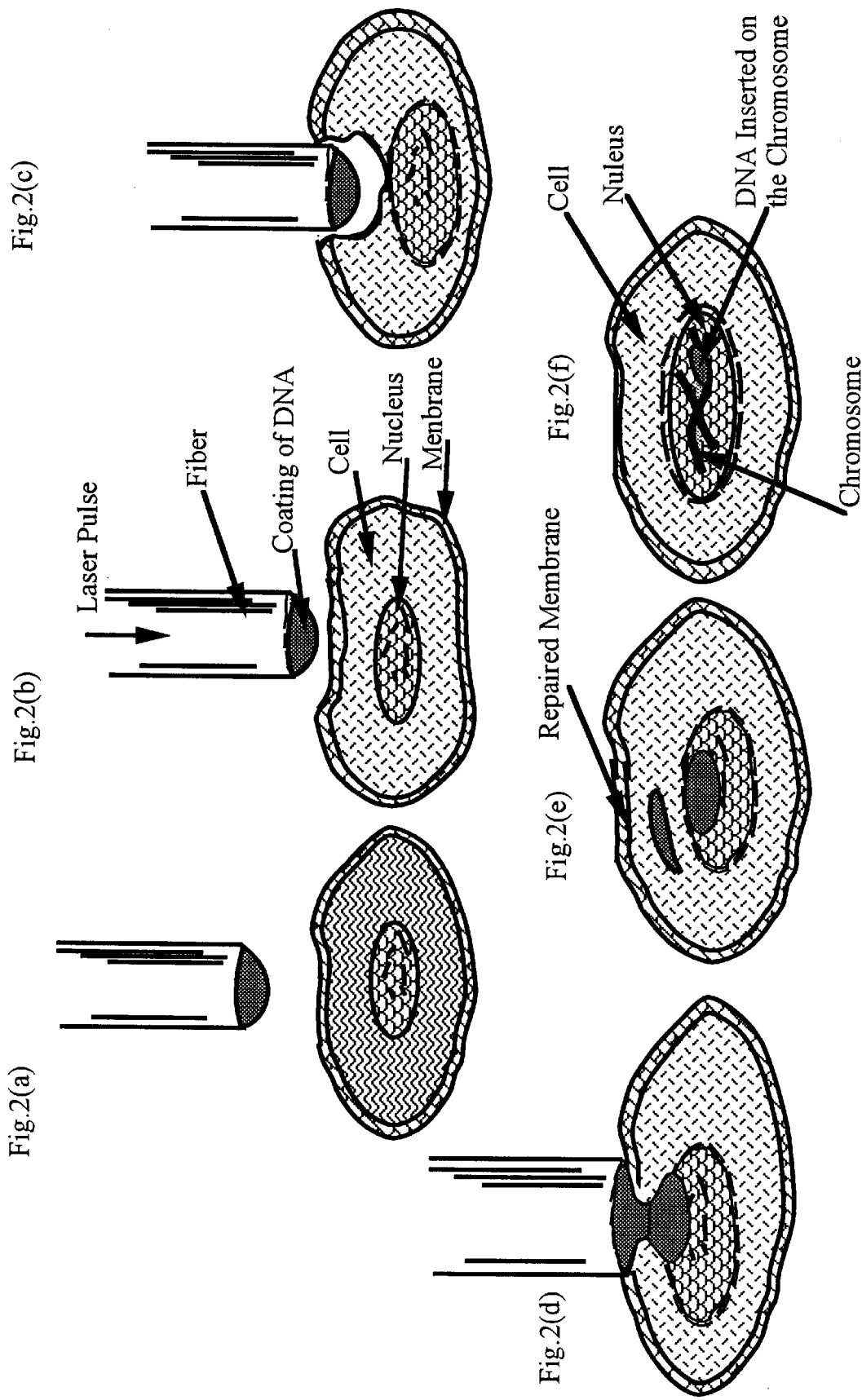

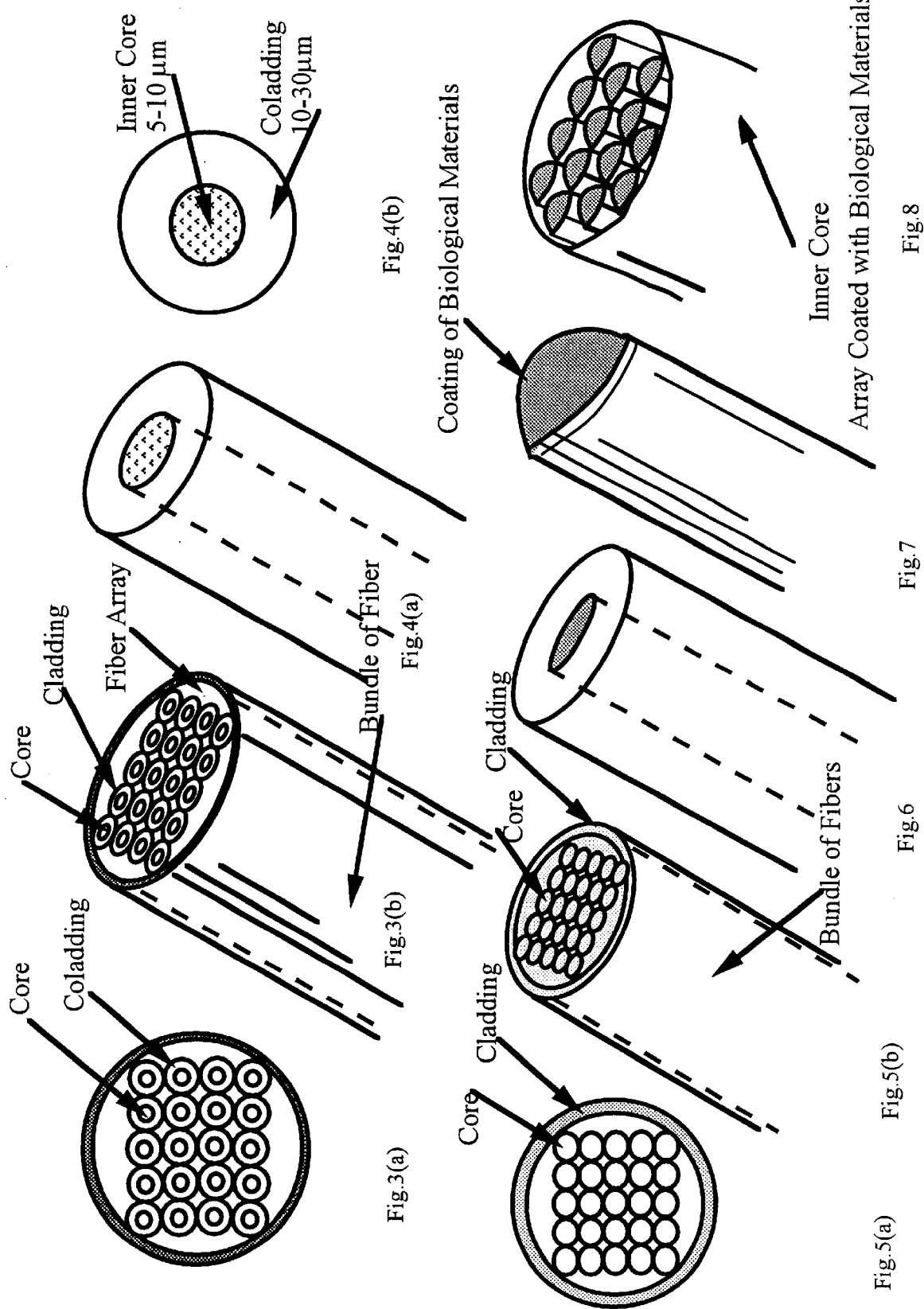

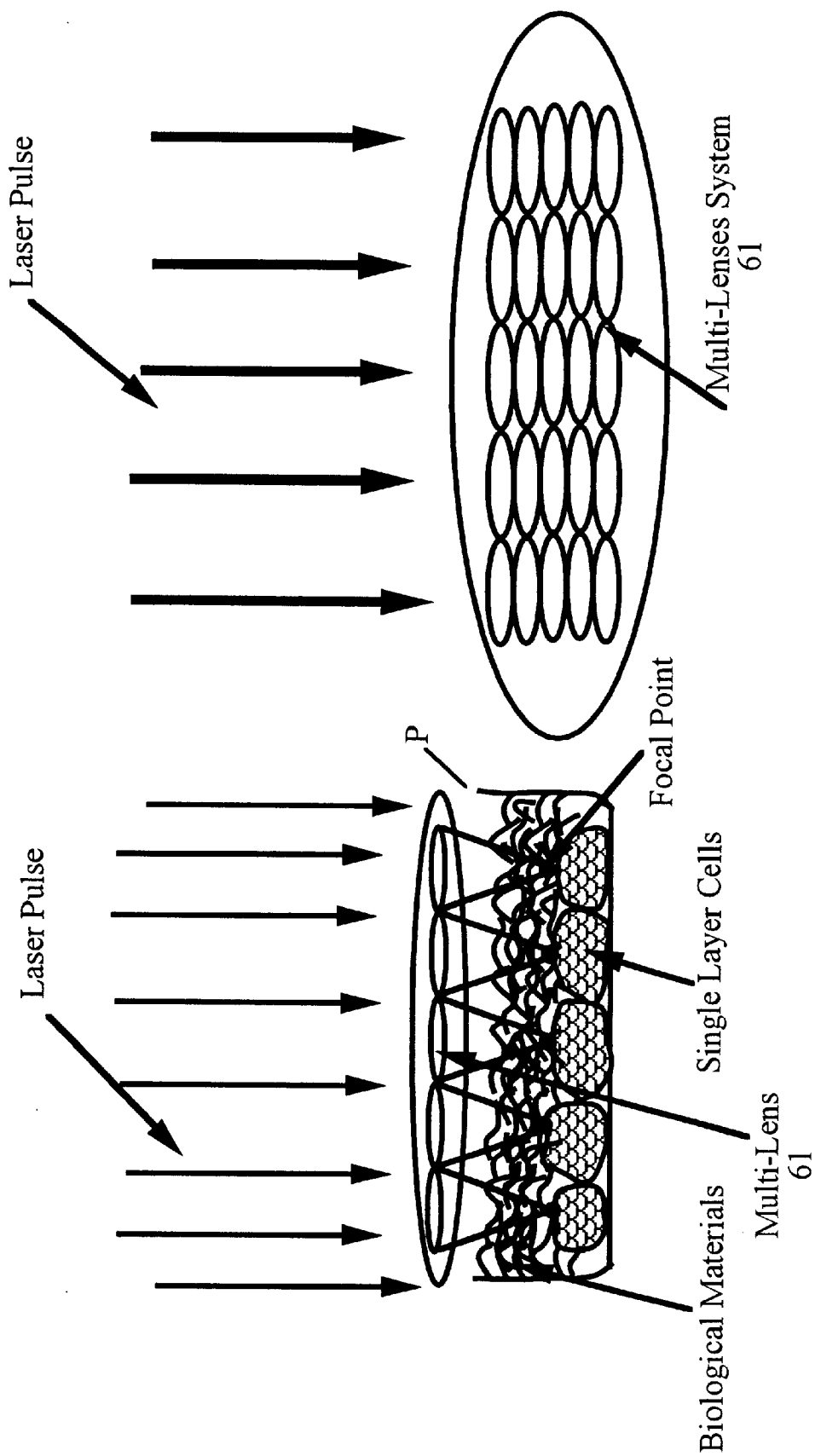

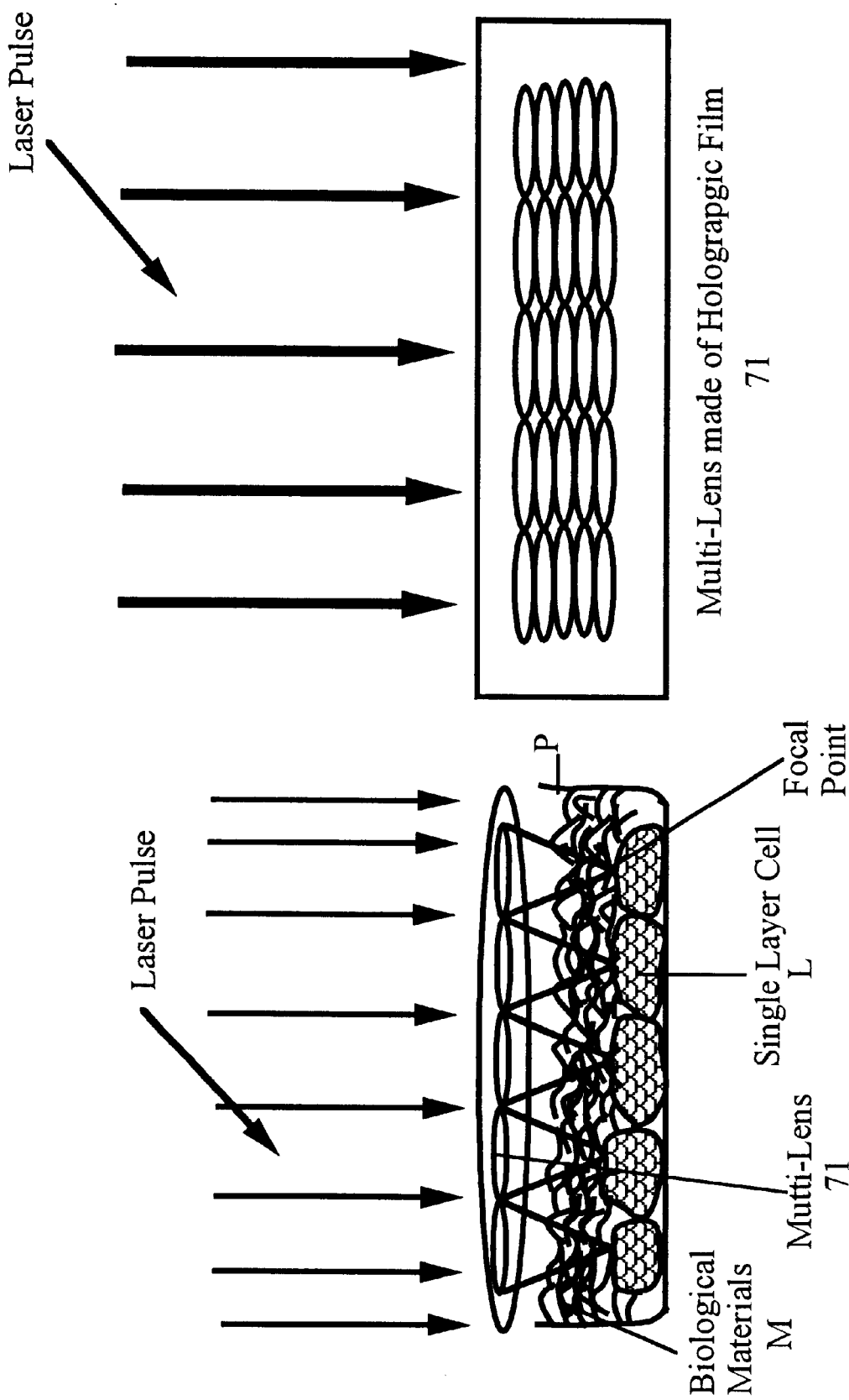

US 6,346,101 B1

PHOTON-MEDIATED INTRODUCTION OF BIOLOGICAL MATERIALS INTO CELLS AND/OR CELLULAR COMPONENTS

This application is a continuation of application(s) Ser. No. 08/584,695 filed on Jan. 11, 1996, which in turn is a continuation of U.S. Ser. No. 08/093,565, filed on Jul. 19, 1993 now abandoned.

The present invention relates to a new and novel technique for introducing biological materials, such as nucleic acids, proteins and the like, into cells and/or cellular components, such as cell nuclei.

As the scientific community's understanding of the field of molecular biology has grown over the last several years, so has interest in manipulating the biological processes that normally take place within individual cells. An active field of this endeavor is the field of recombinant DNA technology. Recombinant DNA technology typically involves altering the naturally-occurring DNA content of a cell, by addition, subtraction and/or substitution of DNA fragments, so that different proteins are encoded by the cell's DNA.

One well-known technique for introducing exogenous DNA fragments into target cells is called "transformation" and typically involves inserting the exogenous DNA fragments into genetic vehicles, such as plasmids or suitable types of viruses, which are capable of traversing cell membranes. One shortcoming of this technique is that little control can be exerted over which target cells will actually come into contact with the vehicles and, consequently, receive exogenous DNA.

Another well-known technique for introducing exogenous DNA fragments and other biological materials into target cells is known as "microinjection." Microinjection, which is typically performed under a phase-contrast microscope, typically involves filling a glass microcapillary with the desired materials and injecting the materials into the cytoplasm of a target cell with the air of a micromanipulator and gentle air pressure exerted by a syringe connected to the capillary. Although microinjection overcomes the limitation discussed above in connection with transformation in that tight control can be exerted over the selection of a specific target cell, microinjection suffers from being very time-consuming and requiring a high degree of skill. In addition, vibration, grounding, electrostatic shielding, temperature control, optics, recording equipment, and fabrication of microtools can all be complicating factors.

Another technique that has been suggested in the past has been to coat the tip of a projectile with a biological material to be introduced into a cell and then directing the projectile into the cell.

SUMMARY OF THE INVENTION

It is an object of the present invention to provide a new and novel technique for introducing biological materials into cells and/or cellular components.

It is another object of the present invention to provide a technique as described above which overcomes at least some of the limitations described above in connection with the above-noted existing techniques.

Accordingly, in keeping with the teachings of the present invention, there is disclosed in one embodiment of the present invention a method for introducing desired biological materials into a target cell and/or a target cellular component, the method comprising the steps of (a) providing a light supply, said light supply including an optical fiber having an output end; (b) contacting said output end of said optical fiber with desired biological materials; (c) orienting said output end of said optical fiber towards a target cell and/or a target cellular component; and (d) transmitting a pulse of light of an appropriate energy level through said optical fiber so as to impart momentum to the desired biological materials disposed at said output end and so as to cause ablation of the membrane of the target cell and/or of the target cellular component, whereby the biological materials enter the target cell and/or the target cellular component through the ablated membrane.

The present invention is also directed to a system for carrying out the aforementioned method.

Additional objects, as well as features and advantages, of the present invention will appear from the description to follow. In the description, reference is made to the accompanying drawings which form a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts:

FIGS. 2(a) through 2(f) are schematic views illustrating the photon-mediated introduction of biological materials into cells and/or cellular components as accomplished by the system of FIG. 1;

FIGS. 3(a) and 3(b) are schematic views of one type of optical fiber bundle which may be used in the system of FIG. 1;

FIGS. 4(a) and 4(b) are schematic views of one of the optical fibers shown in FIGS. 3(a) and 3(b);

FIGS. 5(a) and 5(b) are schematic views of another type of optical fiber bundle which may be used in the system of FIG. 1;

FIG. 6 is a schematic view of the optical fiber shown in FIGS. 4(a) and 4(b) with a coating of biological materials applied thereto;

FIG. 7 is a schematic view of one of the optical fibers shown in FIGS. 5(a) and 5(b) with a coating of biological materials applied thereto; and FIG. 8 is a schematic view of the optical fiber bundle shown in FIGS. 5(a) and 5(b) with a coating of biological materials applied to the core of each fiber thereof;

FIG. 10 is a schematic view illustrating an alternative method for the photon-mediated introduction of biological materials into cells and/or cellular components;

FIG. 11 is a schematic view showing the multi-lens system of FIG. 10 in isolation;

FIG. 12 is a schematic view illustrating another alternative method for the photon-mediated introduction of biological materials into cells and/or cellular components; and FIG. 13 is a schematic view showing the multi-lens system of FIG. 12 in isolation.

DETAILED DESCRIPTION OF PREFERRED EMBODIMENTS

The present invention is directed to a new and novel technique for introducing biological materials into a cell and/or into a cellular component. (For purposes of simplicity, cells and cellular components will hereinafter be referred to representatively as "cells.") The technique is premised on the discovery that photonic energy can be used to transport biological materials through a cell membrane by ablating a portion of the cell membrane and by imparting sufficient momentum to the biological materials to cause them to enter the cell through the ablated cell membrane.

According to one embodiment of the technique, biological materials are coated onto the output end of an optic fiber, the output end of the fiber is aimed at a cell, and a pulse of light of sufficient energy is transmitted through the fiber to drive the biological materials off the end of the fiber and to ablate a portion of the cell membrane, whereby a portion of the biological materials is then driven through the ablated portion of the membrane.

In other embodiments of the technique, biological materials are layered over a single layer of cells in a petri dish or the like. Different types of lenses are used to focus light emitted from a laser or the like onto the cells. Once ablation of the cells' membranes occurs, the biological materials layered on top of the cells enters through the ablated membranes.

The basic system for performing the technique according to the first embodiment described above preferably comprises means for generating ultrafast laser pulses, optical fibers designed to deliver the laser pulses and to carry the biological materials, and a real-time record and analysis system.

The biological materials may be, as examples, DNA, nucleai acids, RNA, proteins, genes, enzymes antibiotics, chemical, virus, sugars, insulin, vaccines, drugs, vitamins and immunoglobins.

More specifically, the optic fiber preferably comprises an array of optic fibers, with each individual fiber of the array having an inner core with a diameter of $2\mu$ to $10\mu$ and cladding whose diameter depends on the diameter of the targeted cell (e.g. typically $30\mu$ or more). For animal and human cells which usually have a diameter around $30\mu$, the optical fiber inner core diameter may be about $2\mu$ to $20\mu$, with cladding of about $30\mu$ in diameter. For plant cells, cell size is in the submillimeter range so one may use optical fiber inner core diameters greater than $10\mu$, with cladding in the millimeter range. Either the entire output end or the inner ring core of the fiber may be coated with the biological materials one wishes to introduce into the cell.

Figure 1:
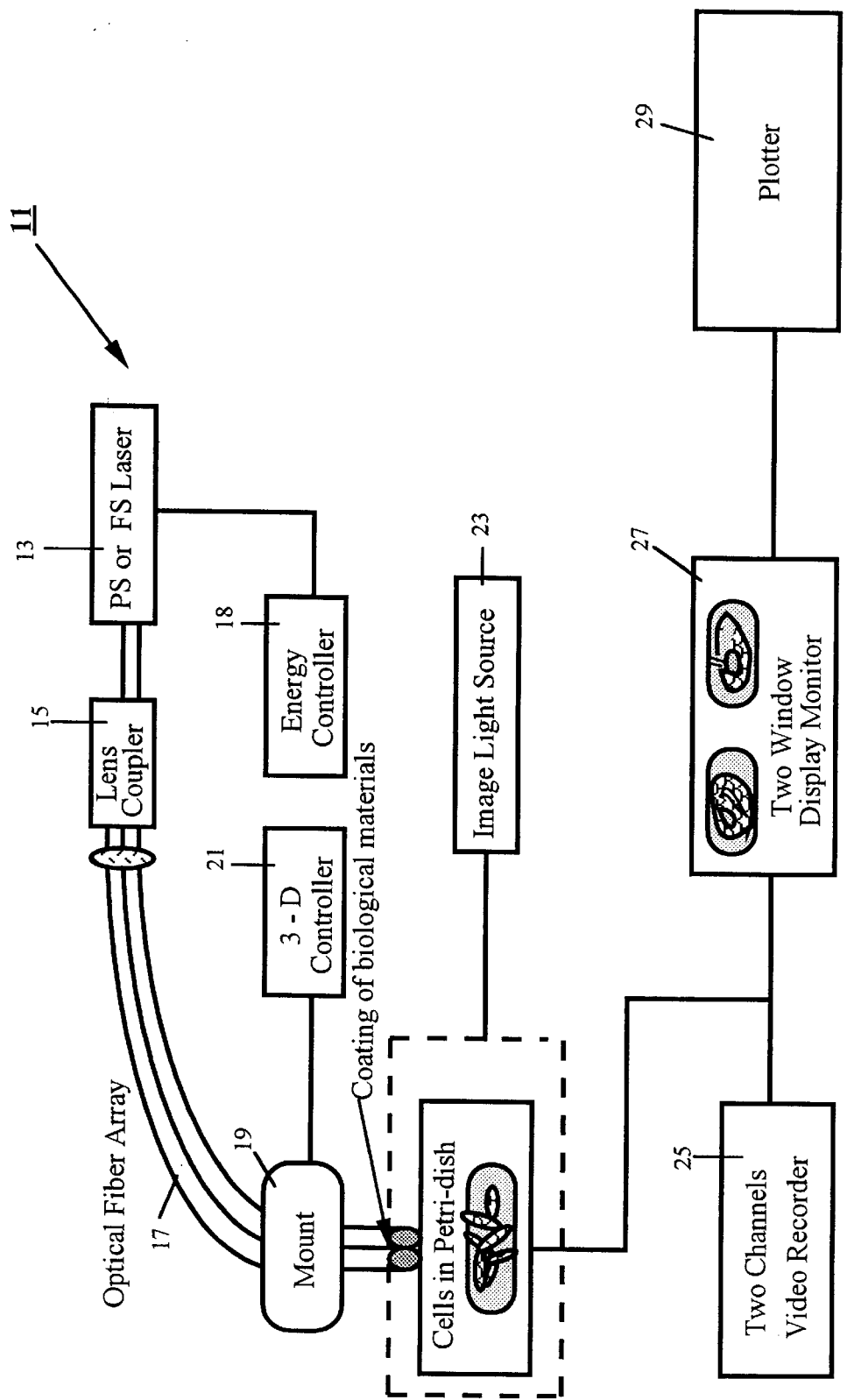
FIG. 1 is a schematic diagram of one embodiment of a system for introducing biological materials into a target cell and/or a target cellular component according to the teachings of the present invention.

Referring now to FIG. 1, there is shown one embodiment of a system constructed according to the teachings of the present invention for introducing biological materials into a cell, the system being represented generally by reference numeral 11.

System 11 includes a laser source 13 capable of generating picosecond (ps) or femtosecond (fs) light pulses having a wavelength in the UV region (e.g. 300 nm, 353 nm), the visible region (e.g. 530 nm, 620 nm or dye emission) or infrared region (e.g. 0.7 to 1.35 um, 1060 nm, 1270 nm or 1500 nm) with power in the range of approximately $5 \times 10^{10}$ W/cm$^2$ (the exact power output being controllable by an energy controller 18).

A lens coupler 15 is used to couple the output of laser source 13 to an optical fiber array 17. As will hereinafter be described in greater detail, optic fiber array 17 serves two purposes: (1) it transmits light pulses from source 13 to one or more target cells; and (2) it holds the biological materials one wishes to introduce into the target cell(s) on the output ends of its individual fibers.

Fiber array 17 is attached to a mount 19 which, in turn, is coupled to a 3-D controller 21. In this manner, the output of fiber 17 can be pointed in any desired direction, depending on the location of the target cells C.

An image light source 23 is used to illuminate the target cells C from both the vertical direction and the side direction for recording by a video image camera 25 and viewing on a display monitor 27 (and/or plotter 29). In this manner, the injection process can be continuously observed through the video display monitor 27. The target cell C may be, as examples of a plant, a human, sperm or ovaries.

Referring now to FIGS. 2(a) through 2(f), a series of schematic views are shown illustrating conceptually how system 11 is able to introduce biological materials into cells and/or cellular components through photon-mediated technology. In FIG. 2(a), a single optical fiber with biological materials applied to its output end is brought into proximity with an individual mammalian cell. The fiber is appropriately sized to correspond to the size of the target cell.

In FIG. 2(b), the fiber tip and the biological materials applied thereto are brought into contact with the target cell. In FIG. 2(c), a light pulse is emitted from the fiber, causing ablation of a portion of the cell membrane. In FIG. 2(d), the biological materials are driven off the end of the fiber (due to adsorption of some of the photonic energy emitted from the fiber) into the target cell through the ablated membrane.

In FIG. 2(e), the cell membrane is shown after it has repaired itself, with some of the injected biological materials having entered the cell nucleus. In FIG. 2(f), some of the biological materials which have entered the cell nucleus (in this case, DNA) are shown inserted on a chromosome.

Nucleic acids can be coupled to light-emitting dyes like acridine orange (AO) to monitor their location within a cell after they have been introduced thereinto in accordance with the technique of the present invention.

Referring to FIGS. 3 through 8, there are shown various schematic views of optic fibers and optic fiber bundles, both with and without biological materials applied thereto, which may be used in system 11.

Figure 9B:
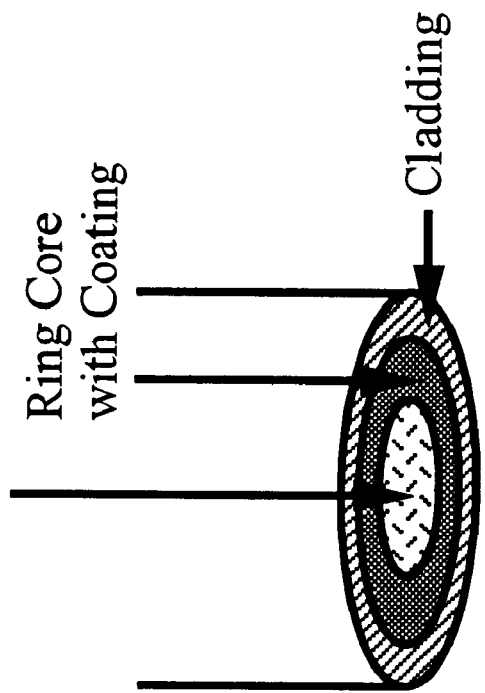
FIGS. 9(a) and 9(b) are schematic views of a specifically designed optical fiber which may be used in the system of FIG. 1.
Figure 9A:
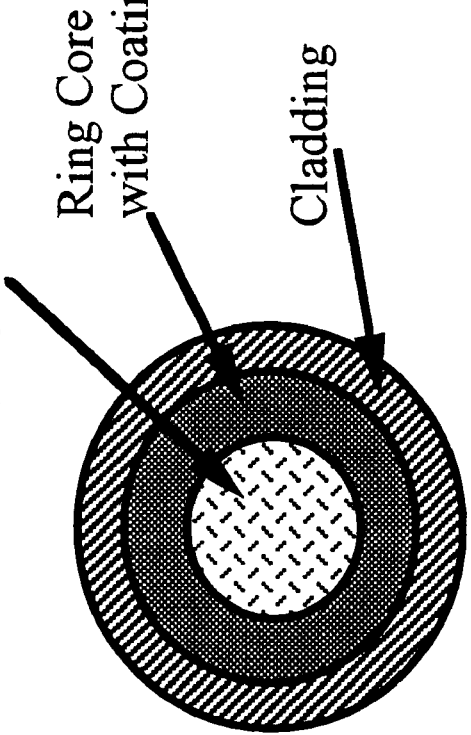

In FIGS. 9(a) and 9(b), there are shown schematic views of a specifically designed optical fiber 51 which may be used in the system of FIG. 1. As can be seen, fiber 51 includes a regular inner core 53, a ring core 55 and cladding 57. In use, the biological materials are preferably applied to ring core 55 so that, after a laser pulse is emitted from inner core 53 and opens a small hole in the target cell membrane, the biological materials are driven off ring core 55 by a laser pulse emitted therethrough.

Referring now to FIGS. 10 and 12, there are shown alternative methods for the photon-mediated introduction of biological materials into cells. In each of the alternative methods, the target cells are spread in a single layer L on a petri-dish P or the like, with the biological materials M one wishes to introduced thereinto being spread on top of the target cells. A multilens system (represented in FIGS. 10 and 11 by reference numeral 61 and in FIGS. 12 and 13 by reference numeral 71) is used to focus a laser pulse onto the layer of cells at certain specified locations to ablate the cell membranes thereat. Once the cell membranes have been ablated, the biological materials disposed thereon are permitted to enter the cells.

The embodiments of the present invention are intended to be merely exemplary and those skilled in the art shall be able to make numerous variations and modifications to it without departing from the scope and spirit of the present invention. The above and other such variations and modifications are intended to be merely within the scope of the present invention as defined in the appended claims.

What is claimed is:

1. A method for introducing desired biological materials into a target cell, said method comprising the steps of:
   (a) laying the desired biological materials on top of the target cell;
   (b) then, irradiating the target cell with a pulse of light having a duration of approximately $10^{-12}$ to $10^{-15}$ seconds and having an output power of approximately $5 \times 10^9$ W/cm$^2$ to $5 \times 10^{13}$ W/cm$^2$ so as to cause ablation of the membrane of the target cell without causing ablation of the biological materials, whereby at least some of the biological materials disposed on top of the target cell enter the target cell through the ablated membrane.

2. A method for introducing desired biological materials into a target cell, said method comprising the steps of:
   (a) providing a light supply, said light supply including an optical fiber having an output end;
   (b) contacting said output end of said optical fiber with the desired biological materials;
   (c) aiming said output end of said optical fiber at a target cell; and
   (d) transmitting a pulse of light having a duration of approximately $10^{-12}$ to $10^{-15}$ seconds and having an output power of approximately $5 \times 10^9$ W/cm$^2$ to $5 \times 10^{13}$ W/cm$^2$ through said optical fiber so as to impart momentum to the desired biological materials disposed on said output end of said optical fiber in order to drive the biological materials off said output end of said optical fiber and towards the target cell and so as to cause ablation of the membrane of the target cell without causing ablation of the biological materials, whereby at least some of the biological materials enter the target cell through the ablated membrane.

* * * * *